United States Patent [19]

Kanotscher

[11] Patent Number: 4,948,368
[45] Date of Patent: Aug. 14, 1990

[54] MIXING DEVICE FOR USE IN DENTISTRY

[76] Inventor: Alexander Kanotscher, Högenauerstrasse 3, A-5280 Braunau am Inn, Austria

[21] Appl. No.: 313,653

[22] Filed: Feb. 21, 1989

[30] Foreign Application Priority Data

Feb. 18, 1988 [AU] Australia .................................. A393

[51] Int. Cl.⁵ ............................................. A61G 1/14
[52] U.S. Cl. ........................................ 433/77; 433/79; 206/369
[58] Field of Search ......................... 433/49, 77, 79; 206/63.5, 368, 369

[56] References Cited

U.S. PATENT DOCUMENTS 4,180,159 12/1979 Tanaka ............................... 206/63.5
4,353,694 10/1982 Pelerin .................................... 433/77

FOREIGN PATENT DOCUMENTS 2595940 9/1987 France ................................. 433/49

Primary Examiner—John J. Wilson
Attorney, Agent, or Firm—Herbert Dubno

[57] ABSTRACT

A mixing device for molding compositions for use in dentistry has a housing into which and from which a trough plate and the underlying tray can be displaced like a drawer. A mat of bibulous material substantially completely fills the tray beneath the trough plate and delivers water in a controlled manner through passages traversing the trough plate and leading to the troughs. A vessel containing the moisturizing liquid is placed on the housing and is connected by a conduit with the tray, the conduit including a valve for controlling flow to the tray.

12 Claims, 1 Drawing Sheet

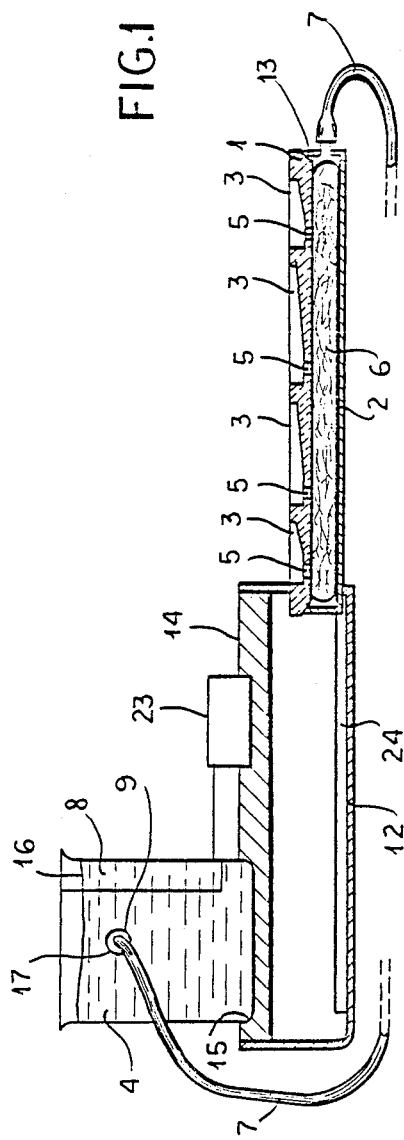
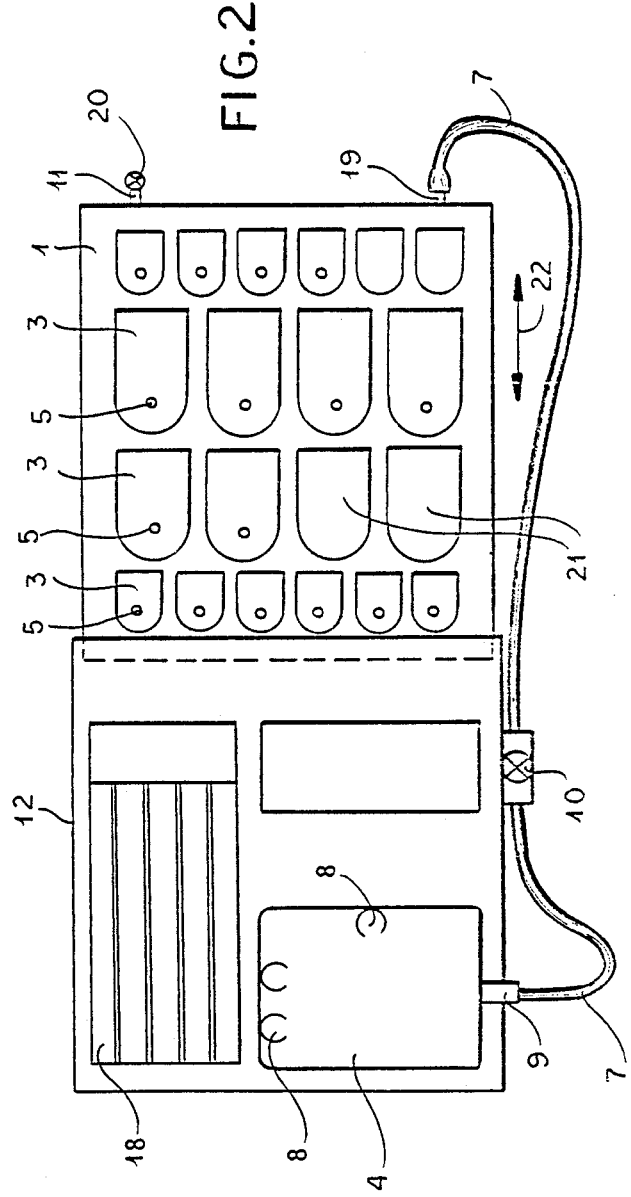

MIXING DEVICE FOR USE IN DENTISTRY

FIELD OF THE INVENTION

My present invention relates to a mixing device for molding compositions for use in dentistry and, more particularly, to a mixing device for this purpose which can accommodate a number of mixing troughs and can ensure a continuous moistening of the compositions which can be formed or mixed in several troughs.

BACKGROUND OF THE INVENTION

Molding compositions, generally in the form of ceramic masses, must be fabricated in dental technology for a variety of purposes and in accordance with a variety of criteria, especially for the formation of dental prostheses or for the filling of regions in dental prostheses or elsewhere in the dental arcade. Criteria such as texture, color, bonding capabilities and material selection are all important. It is thus understandable that mixing plate systems have been provided heretofore which have a number of troughs which must be supplied by a moisturizing source in a continuous manner to prevent premature drying out of the various mixtures which can have different compositions in the troughs, depending upon the several criteria.

Among the earlier systems is an arrangement in which a porous wicking trough plate is provided which is mounted in a water bath in a tray. In this system, the water level must be carefully controlled so that the underside of the porous trough plate is continuously wetted with water. Adjustment of the water level is effected by addition of water and, since such addition must be done manually and with care, use of the mixing device is time-consuming and prone to problems since it is not difficult to inadvertently add water above the desired level and thereby cause an excessive influx of water into the troughs and damage to the mixtures therein. Furthermore, should the level drop below the desired level, moisturizing of the compositions may come to a sudden halt to the detriment of the compositions which rapidly dry out.

In another earlier mixing arrangement, a water reservoir is provided in a tray beneath the trough plate and individual wicks are provided to carry water from the reservoir through holes in the plate into the troughs when the contents of the troughs can thereby be moistened.

In this system as well, the level of liquid must be maintained with precision to ensure a constant and uniform moistening of the compositions and the direct connection of the reservoir with the mixing plate entails a host of disadvantages. For example, any impact delivered to the apparatus, e.g. as a result of mixing, can give rises to waves in the reservoir and can result in changes in the moistening effect. Such waves damp out only slowly and hence the system is prone to nonuniformities.

OBJECTS OF THE INVENTION

It is, therefore, the principal object of the present invention to provide a mixing device for molding compositions for use in dentistry which can ensure a uniform moistening of the molding or casting compositions without time-consuming precision operations to maintain the moistening action.

Another object of the invention is to provide a mixing device which obviates the drawbacks enumerated above.

Still another object of my invention is to provide a compact, easily handled and easily used improved mixing device for the purposes described which is not sensitive to shocks and does not require constant monitoring of a water level in a tray.

SUMMARY OF THE INVENTION

These objects and others which will become apparent hereinafter are attained, in accordance with the invention, in a mixing device for molding compositions for use in dentistry which comprises:

a support formed with an upwardly open tray;

a mixing plate extending across the tray and formed with a multiplicity of upwardly open mixing troughs adapted to receive different compositions, each of the troughs having at least one downwardly opening throughgoing passage;

a mat of a bibulous wicking material received in the tray and underlying the plate whereby moisture can be communicated to the troughs from the mat through the passages;

a liquid container on the support at a level above the tray;

a conduit connecting the container with the tray for feeding a moistening liquid to the mat from the container; and an adjustable flow controller along the conduit for controlling flow of the liquid from the container to the tray.

According to the invention, therefore, in the tray or pan which receives the trough plate, there is provided a mat of bibulous wicking material, especially and preferably a foam-like fleece, while a liquid vessel or container whose liquid level is higher than that of the plane of the trough plate is connected with the tray by a conduit which includes an adjustable flow controller valve, especially a variable frequency dropper or droplet-forming device.

In the space between the walls of the tray and the trough plate, therefore, the hydrostatic pressure of the moistening liquid, usually water, is maintained as a consequence of the fact that the liquid level in the container or reservoir lies above the aforementioned plane so that the bibulous material is continuously moistened and wetted by the water and uniformly transfers moisture to the troughs, but variations in the liquid level do not affect the transfer of moisture to the troughs because the transfer is effected exclusively by the fully saturated bibulous mat.

The tray itself does not contain any water so that shaking of the device does not create waves which can affect the moistening.

The flow rate through the conduit after initially filling and saturation can be very small and can be controlled by a flow control member cap of continuously passing small quantities of water in the droplet range. The flow control element can utilize a squeeze-type cock, an eccentric valve arrangement or any similar flow-control device.

It has been found to be advantageous to have the mat substantially completely fill the tray beneath the trough plate thereof. In this case, no loose liquid can be found anywhere in the tray.

According to another feature of the invention, the tray can be provided with a closable overflow which can be used or opened during the initial period of a high flow rate of the flow controller for the initial filling of the tray with water, the filling being effected until water runs from the overflow. The overflow may then be closed and the flow-control valve similarly closed to allow the mat to soak up the water. The flow-control valve can then be adjusted to admit water to the tray to replace water loss from the saturated mat.

It has been found to be especially advantageous to connect the tray and the trough plate in a fluid-tight manner along the perimeters thereof.

According to another feature of the invention, the tray and the trough plate are provided in the form of a drawer slidable into and out of a housing which can constitute the support for the liquid vessel or container. Indeed, to increase the number of troughs available for mixing of the composition, a plurality of such drawers may be provided in a common housing, the trough plates being covered by cover plates or mixing plates which are not intended to be moistened.

The housings can also be conveniently stacked if desired.

Since the troughs in the trough plate can lie in mutually parallel rows, the tray and plate need only be withdrawn from the housing or slid back into the housing to expose only those rows of troughs in use.

As has already been noted, it is advantageous to mount the liquid container on the housing. The housing can also be provided with troughs for mixing tools, spatulas, pipets, brushes and the like. Hence the mixing device can be a compact unit readily accessible to the technician and occupying a minimum of space.

It has also been found to be advantageous to provide the liquid container or vessel with holders for suspending pipets, mixing pipets and brushes in the liquid in the container.

To prevent sediment from passing into the tray in this case, the connection between the container and the conduit can be located in the upper half of the container wall. When instruments are suspended in the liquid, therefore, there is both an automatic cleaning and moistening of the instruments on the compact unit without any impediment to the supply of moisturizing liquid to the troughs.

It has also been found to be advantageous to provide a filter on the container, in the conduit or at the connection between the conduit and the tray. The conduit can be a plastic (synthetic resin) tube and the fittings at the container and the tray may be tubular fittings formed on the walls of the container and the tray over which the plastic tubing is forced.

BRIEF DESCRIPTION OF THE DRAWING

The above and other objects, features and advantages of the present invention will become more readily apparent from the following description, reference being made to the accompanying drawing in which:

FIG. 1 is a diagrammatic vertical section through a mixing device according to the invention; and FIG. 2 is a top plan view thereof with the mixing plate and tray fully extended.

DESCRIPTION

From the drawing it will be apparent that the trough plate 1 fits like a cover onto a tray 2 and that the plate 1 and the tray 2 are sealed together at 13 along the perimeters of the tray and the trough plate.

The trough plate 1 can be composed of ceramic, porcelain or preferably of glass. The plate 1 is provided with troughs 3 in which respective dental molding compositions can be mixed. The customary proportion method is to add a measured amount of a pulverulent or pasty base material to the trough and then to add water, e.g. distilled water from a container or reservoir 4, to the composition by means of a pipet which can also be used as a mixing rod. The mixture is formed and retained in the respective trough 3 until it is used.

To prevent drying out of the mixed compositions, the troughs 3 are moistened from below.

For this purpose, the troughs 3 are provided with throughgoing passages 5 which open into the tray 2 below the trough plate 1.

The tray 2, according to the invention is substantially completely filled with a bibulous material 6, for example, a fleece mat.

A conduit 7 in the form of a flexible plastic tube, can open into the tray 2 and can be supplied with water from the vessel 4 which is mounted upon a support 12 having an upper surface 14 containing a recess 15 to receive the container 4 of complementary shape.

The liquid level 16 in the container is above the level of the trough in the trough plate 1.

The vessel 4 is provided with holders, such as clips 8 to allow pipets, spatulas or brushes to be releasably held below the water level and thereby clean and moisten these tools which are customarily used in dental techniques utilizing the unit of the present invention.

As a result, at the region of the bottom of the vessel 4, there can be some turbidity resulting form materials washed off the suspended tools. As a consequence, the connection for the tube 7 is provided at 17 in the upper half of a container wall rather than at the bottom thereof.

As is especially apparent form FIG. 2, the surface 14 can be provided with additional troughs 18 for receiving the various tools. The conduit 7 also includes a filter 9, here shown to be at the container wall but also disposable anywhere else along the conduit, e.g. at the fitting 19 connecting the tube to the tray.

The conduit also includes a flow regulator 10. The flow regulator serves to control the rate at which water is supplied by gravity from the container 4 to the tray. Initially the valve 10 is held wide open to fill the tray until the liquid emerges from the overflow 11 closed by a valve 20. The overflow valve 20 is then closed and the bibulous material 6 fully takes up the water so that the valve 10 can then be closed to deliver only sufficient water to the bibulous material 6 to maintain it saturated.

Since the tray 2 and the plate 1 are sealed together all around their contacting edges, the water exudes slowly and is controlled by the valve 10 from the bibulous material into the passages 5 and through the latter to the troughs 3 to maintain the compositions in the respective troughs moisturized without excessive dilution or wetting.

FIG. 2 shows further that not every trough must be provided with a passage 5 and hence the troughs 21 have no such passages and can retain dry material.

Furthermore, it will be apparent that the housing 12 can receive plate 1 and tray 2 in the form of a drawer from which the tray and plate have been shown to be fully extracted in FIG. 1 and into which the tray and plate can be fully inserted by movement in the direction of the row 22.

It will be apparent that the housing can carry not only the tool holder 18 and the vessel 4, but also a sponge 23 as is required by the dental technician. A single housing can receive a plurality of such drawers in individual drawer guides 24 if desired, and, of course, a plurality of housings can be stacked one upon another.

It may be noted that the troughs of the trough plate can have appropriate indicia, e.g. numbers permanently located under the glazing of the plate 1. It is also possible to provide along the edges of the plate indicia as to the mixture compositions, flask numbers of the mixtures or the like to facilitate use of the device. A template can also be provided and can be placed upon the trough plate 1 while the troughs 3 can have corresponding recesses to promote identification. For example, the template can be inscribed with the contents of the various compositions.

I claim:

1. A mixing device for molding compositions for use in dentistry, comprising:
   a support formed with an upwardly open tray;
   a mixing plate extending across said tray and formed with a multiplicity of upwardly open mixing troughs adapted to receive different compositions, each of said troughs having at least one downwardly opening throughgoing passage;
   a mat of a bibulous wicking material received in said tray and underlying said plate whereby moisture can be communicated to said troughs from said mat through said passages;
   a liquid container on said support at a level above said tray;
   a conduit connecting said container with said tray for feeding a moistening liquid to said mat from said container; and
   an adjustable flow controller along said conduit for controlling flow of said liquid from said container to said tray.

2. The mixing device defined in claim 1 wherein said flow controller is a dropper having a variable droplet forming rate.

3. The mixing device defined in claim 1 wherein said mat substantially completely fills said tray below said plate.

4. The mixing device defined in claim 1 wherein said tray is formed with a closable overflow passage.

5. The mixing device defined in claim 1 wherein said plate and said tray are connected in a liquid-tight manner around peripheries of said tray and said plate.

6. The mixing device defined in claim 1 wherein said support includes a housing and said tray and said plate form a drawer receivable in and extendable from said housing.

7. The mixing device defined in claim 1 wherein said support is provided with troughs for receiving stirrers, spatulas, pipettes and brushes.

8. The mixing device defined in claim 1 wherein said container is formed with means for suspending pipettes and brushes in the liquid in said container, said container having an outlet connected to said conduit at an upper half of a wall of said container.

9. The mixing device defined in claim 1 wherein said conduit is formed with a filter.

10. The mixing device defined in claim 1 wherein said container is formed with a filter for said liquid.

11. The mixing device defined in claim 1 wherein said tray is formed with a filter for said liquid at a connection of said conduit therewith.

12. The mixing device defined in claim 1, further comprising a filter between the liquid in said container and said mat in said tray, said container being formed with means for suspending pipettes and brushes in the liquid in said container, said container having an outlet connected to said conduit at an upper half of a wall of said container, said support being provided with troughs for receiving stirrers, spatulas, pipettes and brushes, said flow controller being a dropper having a variable droplet forming rate, said mat substantially completely filling said tray below said plate, said tray being formed with a closable overflow passage, said plate and said tray being connected in a liquid-tight manner around peripheries of said tray and said plate, said support including a housing and said tray and said plate form a drawer receivable in and extendable from said housing.

* * * * *